United States Patent [19]

Dufresne et al.

[11] Patent Number: 4,686,991
[45] Date of Patent: Aug. 18, 1987

[54] ELECTRICAL STIMULATOR FOR BIOLOGICAL TISSUE UTILIZING LINEAR CURRENT OUTPUT CIRCUIT

[75] Inventors: Joel R. Dufresne; Alan P. Dieken, both of St. Paul, Minn.

[73] Assignee: Minnesota Mining and Manufacturing Company, St. Paul, Minn.

[21] Appl. No.: 745,212

[22] Filed: Jun. 17, 1985

[51] Int. Cl.⁴ .............................................. A61N 1/36
[52] U.S. Cl. ................................................... 128/421
[58] Field of Search .................... 128/419 R, 421, 422, 128/423 R

[56] References Cited

U.S. PATENT DOCUMENTS

| | | |
|---|---|---|
| 4,062,365 | 12/1977 | Kameny . |
| 4,232,680 | 11/1980 | Hudleson et al. . |
| 4,237,896 | 12/1980 | Lines ............................... 128/419 R |
| 4,249,537 | 2/1981 | Lee . |
| 4,305,402 | 12/1981 | Katims . |
| 4,363,324 | 12/1982 | Kusserow ....................... 128/419 R |
| 4,406,288 | 9/1983 | Horwinski et al. ................. 128/422 |
| 4,431,000 | 2/1984 | Butler et al. . |
| 4,476,869 | 10/1984 | Bihn . |
| 4,520,825 | 6/1985 | Thompson et al. ................. 128/422 |
| 4,528,984 | 7/1985 | Morawetz et al. .................. 128/421 |
| 4,541,432 | 9/1985 | Molina-Negro et al. ........... 128/421 |
| 4,582,063 | 4/1986 | Mickiewicz et al. ............... 128/421 |

FOREIGN PATENT DOCUMENTS

3301622A1  7/1984  Fed. Rep. of Germany .

OTHER PUBLICATIONS

Petti John, "Behavior Research Methods and Instrumentation", vol. 8, No. 3, Jun. 1976, pp. 287–289.
Buckett et al, "A Flexible Portable Functional Electrical Stimulation System", 36th *ACEMB*, Sep. 12–14, 1983, p. 39.
Empi NMS 712 Command, publication 360073, Rev. A, 1984.
Hogan, "TENS Unit Modulates Output to Evade Body's Adaptive Capability", Design News, Sep. 17, 1984, pp. 114–115.
Stimtech SD Product Pointer, publication No. 216, 6/7/84, 8 pages.
Hogan, "Neuromuscular Stimulator Permits Customized Therapy", *Design News*, pp. 108–110, Sep. 17, 1984.

*Primary Examiner*—William E. Kamm
*Attorney, Agent, or Firm*—Donald M. Sell; James A. Smith; William D. Bauer

[57] ABSTRACT

An electrical stimulator for biological tissue utilizing a linear current output circuit. A digital-to-analog circuit converts a digital output word to an analog value and feeds a current amplifier having negative feedback. The output current of the amplifier is transformer driven through a push-pull transistor network. A reference impedance provides a voltage indicative of the current output which is fed back to an operational amplifier.

10 Claims, 4 Drawing Figures

ELECTRICAL STIMULATOR FOR BIOLOGICAL TISSUE UTILIZING LINEAR CURRENT OUTPUT CIRCUIT

BACKGROUND OF THE INVENTION

The present invention relates generally to electrical stimulators for biological tissue and more particularly to a linear current output circuit for electrical stimulators of biological tissue.

Electrical stimulators providing an electrical stimulus signal are useful for exciting biological tissue. One significant use for electrical stimulators of this type is for transcutaneous electrical nerve stimulation (TENS) which generate carefully controlled electrical stimulus signals which are delivered via a suitable electrode through a patient's skin to underlying biological tissue. The electrical stimulus signals can be utilized for the purpose of masking pain signals within the nervous system, for example, the sensation of pain felt by a patient after surgery. Because of a patient's response to transcutaneous electrical nerve stimulation may vary significantly, a wide range of electrical stimulus parameters must be provided. A second use of electrical stimulators is for neuromuscular stimulation (NMS) in order to initiate or control muscular action in a patient. Since a wide variety of muscular actions are available, again a wide variety of electrical stimulus signals can be provided.

Recently, electrical stimulators for biological tissue have utilized digital electronics. An example of such a digital electrical stimulator internally generates or provides a digital output word or a series of digital output words indicative of an electrical stimulus signal to be generated. However, while the electrical stimulator generates digital output words indicative of the electrical stimulus signal to be generated, the actual electrical stimulus signal to be output to the biological tissue is analog in nature. Therefore, such a digital electrical stimulator must convert the digital output word, or series of digital output words, to an analog electrical stimulus signal. Thus, such a digital electrical stimulator must provide an output stage in which the digital output word, or series of digital output words, is converted to an analog electrical signal.

While the accuracy of the digital output words can be controlled closely and depends upon the number of bits or digits utilized to represent such digital output word, such accuracy is lost if that accuracy cannot be maintained during the conversion process from the digital output word to the analog electrical stimulus signal.

This need is contrasted to most digital to analog output stages, or circuits, which are concerned with achieving only the highest effeciency possible or in maintaining a constant current output without concern for linearity.

SUMMARY OF THE INVENTION

The electrical stimulator of biological tissue of the present invention has a need for a high degree of accuracy and linearity of transformation from the digital output word, or series of digital output words, to an analog electrical stimulus signal. This output circuit for the electrical stimulator must replicate the desired electrical stimulus waveform with a high degree of accuracy.

The present invention provides a biological tissue stimulator having an output circuit being driven by a digital output word. The biological tissue stimulator has an electrode system adapted to be coupled to biological tissue which is to be stimulated and which serves as a load to the electrical stimulator. A linear digital-to-analog converter is operatively coupled to the output word. A current amplifier is operatively coupled to the digital-to-analog converter and operatively coupled to the electrode system. The current amplifier utilizes negative feedback. In a preferred embodiment, the present invention provides a biological tissue stimulator as above where the current amplifier contains an operational amplifier coupled to the digital-to-analog converter. The operational amplifier has a non-inverting input, an inverting input and an output. The inverting input of the operational amplifier is operatively coupled to the digital-to-analog converter. A compensation circuit is operatively coupled to the operational amplifier. The compensation circuit ensures high frequency stability of the operational amplifier. A transistor network is operatively coupled to the output of the operational amplifier and adapted to be coupled to the electrode system. A reference resistor is operatively coupled to the transistor network the voltage across which is representative of the current being supplied to the electrode system from the transistor network. A feedback path is provided from the reference resistor to the non-inverting input of the operational amplifier.

The present invention also provides a linear current output circuit for a biological tissue stimulator adapted to be driven by digital output word and adapted to be coupled to biological tissue which provides a load for the circuit. The linear current output circuit has a linear digital-to-analog converter operatively coupled to the output word and a current amplifier operatively coupled to the digital-to-analog converter and adapted to be coupled to the load the current amplifier utilizing negative current feedback. In a preferred embodiment, the linear current output circuit has a current amplifier which has an operational amplifier coupled to the digital-to-analog converter. The operational amplifier having an non-inverting input, an inverting input and an output. The inverting input of the operational amplifier is operatively coupled to the digital-to-analog converter. A compensation circuit is operatively coupled to the operational amplifier, the compensation circuit to ensure high frequency stability of the operational amplifier. A transistor network is operatively coupled to the output of the operational amplifier and adapted to be coupled to the load. A reference resistor is operatively coupled to the transistor network, the voltage across which is representative of the current being supplied to the load from the transistor network. A feedback path is coupled from the reference resistor to the non-inverting input of the operational amplifier.

BRIEF DESCRIPTION OF THE DRAWINGS

The foregoing advantages, construction and operation of the present invention will become more readily apparent from the following description and accompanying drawings in which.

DESCRIPTION OF THE PREFERRED EMBODIMENTS

Figure 1:
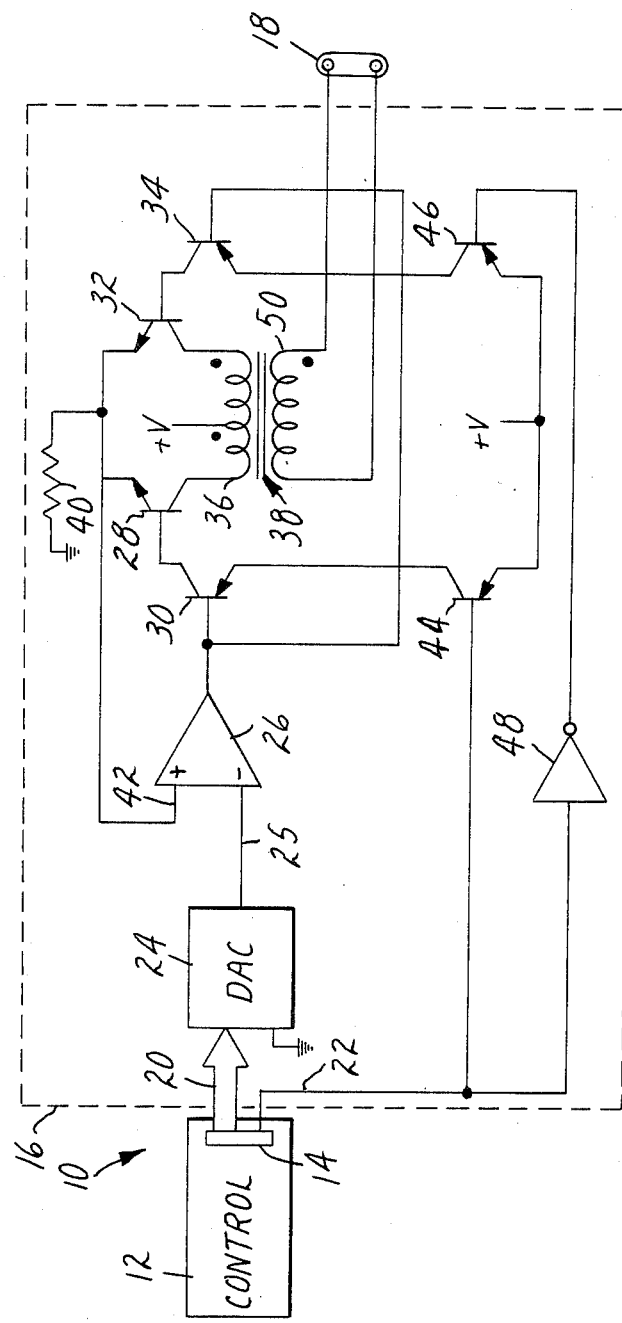
FIG. 1 is a schematic diagram of a preferred embodiment of the present invention.

FIG. 1 illustrates a preferred embodiment of an electrical stimulator 10. The electrical stimulator 10 contains a microprocessor 12 based control portion which generates a series of digital output words 14. The digital output word 14 is to be converted by the linear current output circuit 16 to an analog electrical stimulus signal to be provided to two or more electrodes 18 (hereinafter simply "electrode") which in turn is adapted to be coupled to biological tissue to provide a load for the linear current output circuit 16 and the electrical stimulator 10.

The digital output word 14 is provided to the linear current output circuit 16 by a magnitude portion 20 and a sign portion 22. In a preferred embodiment, digital output word 14 consists of N+2 bits. Magnitude portion 20 then consists on N+1 bits, namely bits 0 through N and the sign portion 22 consists of the bit N+1.

Magnitude portion 20 of digital output word 14 is supplied to the data inputs of digital-to-analog converter 24. Digital-to-analog converter 24 is also connected to a power supply and to electrical ground. The output of digital-to-analog converter 24 is coupled to the inverting input of operational amplifier 26. The output of operational amplifier 26 is used to control two current amplifiers consisting of a first set of transistors 28 and 30 and a second set of transistors 32 and 34. Each set of transistors (namely, transistors 28 and 30 and transistors 32 and 34) act on one-half of the primary winding 36 of transformer 38 providing a push-pull configuration. The center tap of primary winding 36 is connected to an electrical supply. Reference resistor 40 provides a reference voltage indicative of the current flowing through the primary winding 36 of transformer 38. The voltage across reference resistor 40 is fed back to the non-inverting input 42 of operational amplifier 26. The current amplifiers, consisting of transistors 28 and 30 and 32 and 34, are enabled/disabled via transistors 44 and 46 utilizing the sign portion 22 of the digital output word 14. Transistor 44 is coupled directly to the sign portion 22 of digital output word 14 while transistor 46 is coupled indirectly to the sign portion 22 of digital output word 14 through inverter 48. The secondary winding 50 of transformer 38 is coupled to electrode 18 to provide the output from the linear current output circuit 16.

Figure 2:
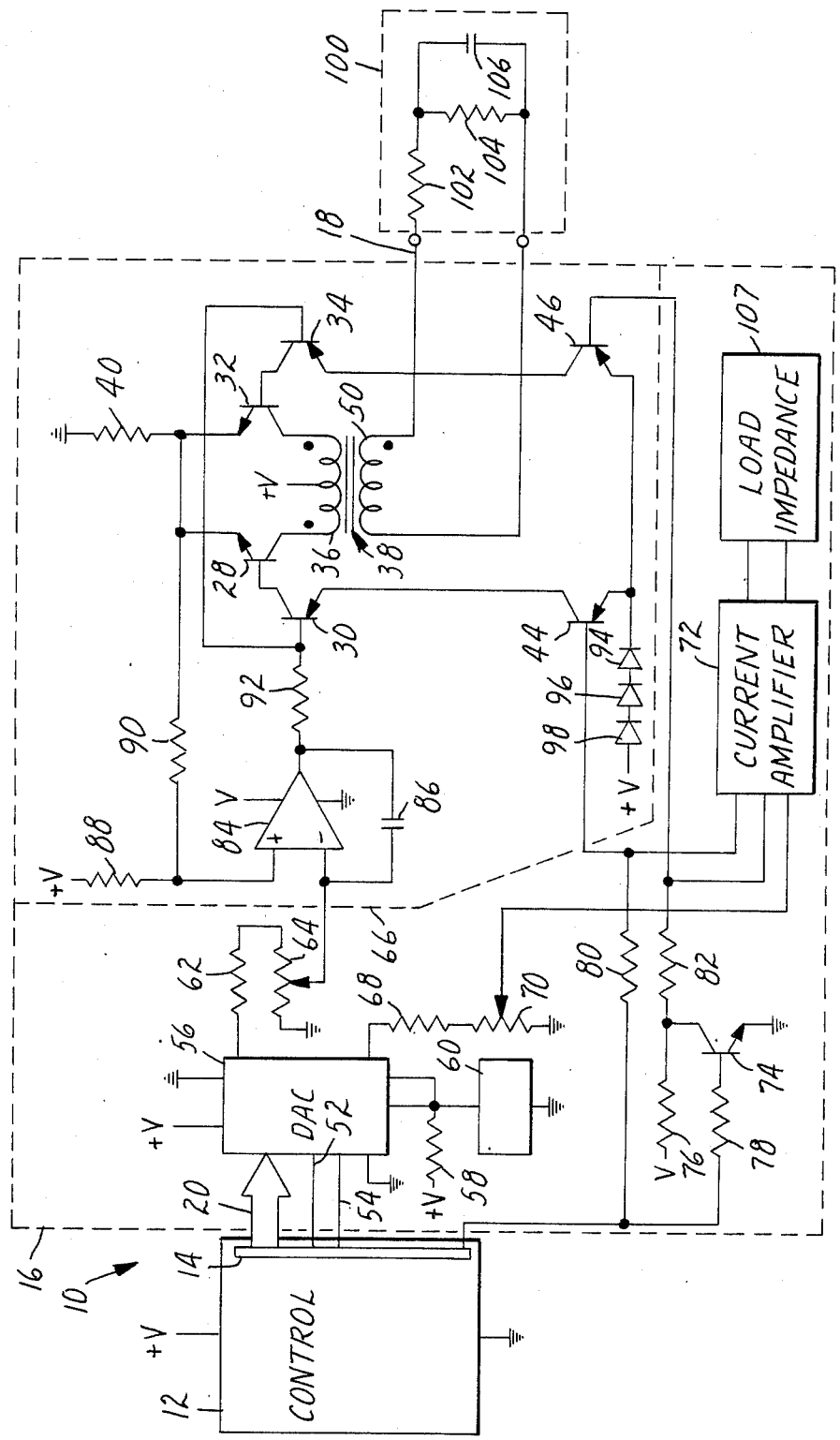
FIG. 2 is schematic diagram of an alternative preferred embodiment of the present invention.

An alternative schematic representation of an electrical stimulator 10 of the present invention is illustrated in FIG. 2. Again, a microprocessor 12 is utilized to provide a digital output word 14, or a series of digital output words 14, to be converted by a linear current output circuit 16 which, in this case, consists of two separate channels. Again, digital output word 14 is separated into a magnitude portion 20 and a sign portion 22. In addition, a digital output word 14 contains a channel select line 52 and a data control line 54. Magnitude portion 20, channel select line 52 and data control line 54 are coupled to digital-to-analog converter 56. Channel select line 52 is utilized to switch between two different output stages contained within digital-to-analog converter 56. Data control line 54 is provided to enable a latching of the magnitude portion 20 of the digital output word 14 into the digital-to-analog converter 56 associated with each channel or stage. A separate latch within the digital-to-analog converter 56 is provided for each of the two output stages. Digital-to-analog converter 56, in addition to being coupled to a power supply and an electrical ground, is coupled to temperature-compensated voltage reference 60. Voltage reference 60 is also coupled to an electrical ground and to an electrical supply through resistor 58. The output of one stage of the digital-to-analog converter 56 is coupled through resistor 62 and potentiometer 64 to a current amplifier 66. Similarly, the other stage of digital-to-analog converter 56 is coupled through a resistor 68 and potentiometer 70 to current amplifier 72. Potentiometers 64 and 70 act as amplitude controls for the respective output channels of digital-to-analog converter 56. Resistor pair 62 and potentiometer 64 act as a voltage divider which matches the maximum output voltage of the digital-to-analog converter 56 to the maximum voltage desired across reference resistor 40.

Current amplifier 66 is similar to the current amplifier illustrated in FIG. 1 but has been expanded upon for more detail. Current amplifier 66 is exemplary of current amplifier 72 which is not illustrated in detail. The sign portion 22 of digital output word 14 is complemented by an inverter consisting of transistor 74 and resistors 76 and 78. Resistor 76 acts as a pull up resistor resistor 78 limits the base current of transistor 74. Note that the inverter consisting of transistor 74 and resistor 76 and 78 are shared by multiple output stages, in this case as exemplified by current amplifiers 66 and 72. Resistors 80 and 82 limit the base drive to current amplifiers 66 and 72.

The output of potentiometer 64 is supplied to the inverting input of operational amplifier 84. Preferably operational amplifier 84 is a high-gain operational amplifier. Still preferably, operational amplifier 84 has a high slew rate and its output stage does not become deeply saturated for output voltages near ground or near power supply potential. Capacitor 86 augments the internal frequency compensation of operational amplifier 84. Voltage offsets at the non-inverting input of operational amplifier 84 can be nulled by voltage divider consisting of resistors 88, 90 and reference resistor 40. The value of resistor 88 can be adjusted, for example by a potentiometer or by trimming, or it may be left at a constant value which reflects the worst case offset for operational amplifier 84. Output of operational amplifier 84 is supplied via resistor 92 to transistors 28, 30, 32 and 34 which operate as in FIG. 1 on the primary winding 36 of transformer 38. Again as in FIG. 1, transistors 44 and 46 enable transistor pairs 28 and 30 and 32 and 34 depending upon the state of the sign portion 22 of digital output word 14. Diodes 94, 96 and 98 connected to electrical power supply ensure that the output of operational amplifier 84 can swing high enough to cut off transistors 30 and 34. Secondary winding 50 of transformer 38 is coupled to electrode 18 and to an exemplary load 100 which is schematically represented by resistance 102, resistance 104 and capacitor 106. Similarly, the output of current amplifier 72 is provided to a load impedance 107.

The path from transistor pairs 28 and 30 and 32 and 34 to reference resistor 40 and through resistor 90 to the non-inverting input of operational amplifier 84 provides a negative feedback path for the current of being applied to the primary winding 36 of transformer 38.

Figure 3:
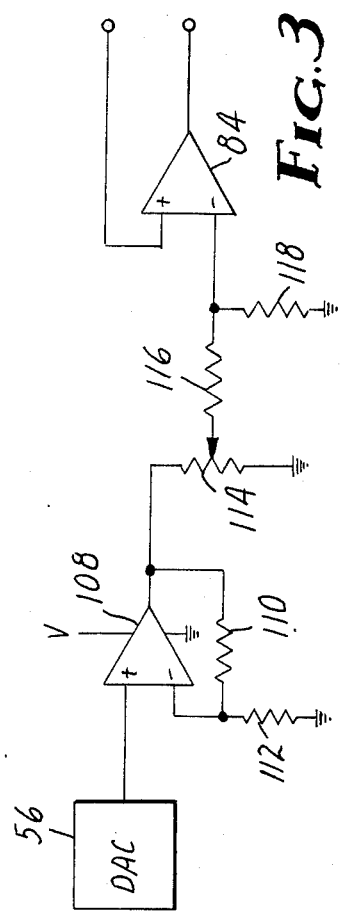
FIG. 3 is an alternative schematic diagram of the amplitude control portion of the schematic diagram of FIG. 2.

An alternative connection between digital-to-analog converter 56 an operational amplifier 84 is illustrated in FIG. 3. An operational amplifier 108 has its non-inverting input connected to the output of digital-to-analog converter 56. Operational amplifier 108 is biased with resistors 110 and 112. Potentiometer 114 and resistors 116 and 118 provide an amplitude control for the signal coupled to the inverting input of operational amplifier 84. The alternative connection illustrated in FIG. 3 may be used advantageously where higher signal levels are required, for example, to overcome noise problems associated with a long physical path between the digital-to-analog converter 56 and the operational amplifier 84. In this circuit, resistors 110 and 112 should be selected such that:

$$\left(1 + \frac{\text{Resistor } 110}{\text{Resistor } 112}\right) \left(\frac{\text{Resistor } 118}{\text{Resistor } 116 + \text{Resistor } 118}\right) = \frac{\text{Resistor } 64}{\text{Resistor } 62 + \text{Resistor } 64}$$

and such that resistors 116 and 118 be much larger than the value of potentiometer 114.

Figure 4:
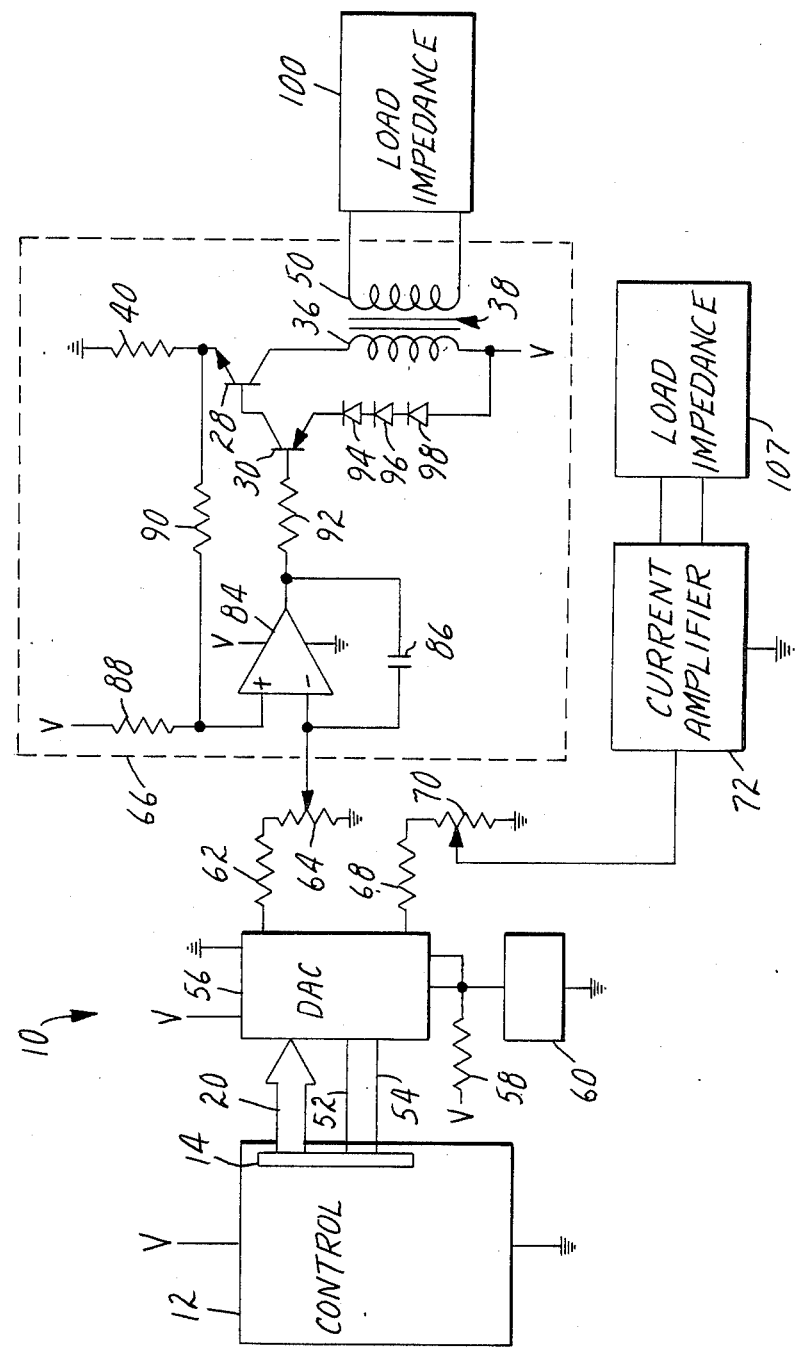
FIG. 4 is a schematic diagram of an alternative preferred embodiment for providing unipolar output.

FIG. 4 represents a schematic diagram of an alternative embodiment of the present invention. The circuit illustrated in FIG. 4 is identical to the circuit illustrated in FIG. 2 with the exception that a unipolar output stage has been constructed utilizing a unipolar current amplifier 66. Also, digital output word 14 need not have a sign portion 22. Current amplifier 66 in FIG. 4 is very similar to current amplifier 66 in FIG. 2 but with the elimination of transistor set 32 and 34 sign selection transistors 44 and 46 and one-half of the primary winding 36 of transformer 38.

Transformer 38 is selected so that a current of at least 100 milliamperes can be driven into load impedence 100 of at least 500 ohms assuming a power supply voltage of at least 4.5 volts DC. Transformer 38 is constructed so that the secondary current faithfully tracks the primary current for wave forms of durations less than 350 microseconds. The preferred values and components utilized in FIGS. 1-4 are specified in the following table I:

| Reference No. | Value or Type No. | Manufacturer |
| --- | --- | --- |
| 12 | Myocare Plus | 3 M |
| 24 | AD7528 | Analog Devices |
| 26 | CA3240A | RCA |
| 28 | ZTX650 | Feranti |
| 30 | 2N3906 | National |
| 32 | ZTX650 | Feranti |
| 34 | 2N3906 | National |
| 38 | Primary:Secondary = 32:640 | Precision |
| 40 | 0.24 | Ohms |
| 44 | 2N3906 | National |
| 46 | 2N3906 | National |
| 56 | AD7528 | Analog Devices |
| 58 | 4.7 Kilohms | |
| 60 | LM336Z2.5 | National Semiconductor |
| 62 | 12 Kilohms | |
| 64 | 10 Kilohms | |
| 68 | 12 Kilohms | |
| 70 | 10 Kilohms | |
| 74 | 2N2222 | Motorola |
| 76 | 100 Kilohms | |
| 78 | 51 Kilohms | |
| 80 | 7.5 Kilohms | |
| 82 | 7.5 Kilohms | |
| 84 | CA3240A | RCA |
| 86 | 100 Picofarads | |
| 88 | 100 Kilohms | |
| 90 | 100 Ohms | |
| 92 | 1 Kilohms | |
| 94 | 1N4148 | Motorola |

-continued

| Reference No. | Value or Type No. | Manufacturer |
| --- | --- | --- |
| 96 | 1N4148 | Motorola |
| 98 | 1N4148 | Motorola |
| 102 | 500 Ohms | |
| 104 | 2.7 Kilohms | |
| 106 | 0.1 Microfarads | |
| 108 | LM358 | National Semiconductor |
| 110 | 100 kilohms | |
| 112 | 100 kilohms | |
| 114 | 10 kilohms | |
| 116 | 360 kilohms | |
| 118 | 50 kilohms | |

Thus, it can be seen that there has been shown and described a novel electrical stimulator for biological tissue utilizing a linear current output circuit. It is to be understood, however, that various changes, modifications, and substitutions in the form of the details of the described invention can be made by those skilled in the art without departing from the scope of the invention as defined by the following claims.

What is claimed is:

1. A linear current output circuit for a biological tissue stimulator receiving a digital output word and for driving said biological tissue which provides a load for said circuit, comprising:
   a linear digital-to-analog converter for receiving said output word;
   an operational amplifier coupled to said digital-to-analog converter, said operational amplifier having a noninverting input, an inverting input and an output, said inverting input being operatively coupled to said digital-to-analog converter;
   compensation circuit means operatively coupled between said inverting input and said output of said operational amplifier for ensuring the high-frequency stability of said operational amplifier;
   transistor network means operatively coupled to said output of said operational amplifier and adapted to be coupled to said load for providing current amplification to said output of said operational amplifier;
   reference resistor means operatively coupled to said transistor network for having a voltage across said reference resistor means which is representative of the current being supplied to said load from said transistor network means; and
   feedback path means coupled to said reference resistor means and to said non-inverting input of said operational amplifier for supplying said voltage across said reference resistor means to said operational amplifier.

2. A linear current output circuit as in claim 1 which further comprises offset circuit means operatively coupled to said operational amplifier for compensating for any input voltage offset of said operational amplifier.

3. A linear current output circuit as in claim 1 further comprising a precision voltage reference source operatively coupled to said digital-to-analog converter which supplies a precision voltage to said digital-to-analog converter.

4. A linear current output circuit as in claim 1 wherein said transistor network means has a bipolar output to said load.

5. A linear current output circuit as in claim 4 wherein said transistor network means comprises a pair of transistors coupled in push-pull arrangement, a center tapped transformer adapted to be coupled to said load, wherein said pair of transistors are coupled to said center-tapped transformer.

6. A biological tissue stimulator having an output circuit receiving a digital output word, comprising:
  electrode means for application to biological tissue which is to be stimulated and which serves as a load to said biological tissue stimulator;
  a linear digital-to-analog converter operatively coupled to said digital output word;
  an operational amplifier coupled to said digital-to-analog converter, said operational amplifier having a noninverting input, an inverting input and an output, said inverting input being operatively coupled to said digital-to-analog converter;
  compensation circuit means operatively coupled between said inverting input and said output of said operational amplifier for ensuring the high-frequency stability of said operational amplifier;
  transistor network means operatively coupled to said output of said operational amplifier and adapted to be coupled to said electrode for providing current amplification to said output of said operational amplifier;
  reference resistor means operatively coupled to transistor network for having a voltage across said reference resistor means which is representative of the current being supplied to said electrode from said transistor network means; and
  feedback path means coupled to said reference resistor means and to said noninverting input of said operational amplifier for supplying said voltage across said reference resistor means to said operational amplifier.

7. A biological tissue stimulator as in claim 6 which further comprises offset circuit means operatively coupled to said operational amplifier for compensating for any input voltage offset of said operational amplifier.

8. A biological tissue stimulator as in claim 6 further comprising a precision voltage reference source operatively coupled to said digital-to-analog converter which supplies a precision voltage to said digital-to-analog converter.

9. A biological tissue stimulator as in claim 6 wherein said transistor network means has a bipolar output to said load.

10. A biological tissue stimulator as in claim 9 wherein said transistor network means comprises a pair of transistors coupled in push-pull arrangement, a center-tapped transformer adapted to be coupled to said load, wherein said pair of transistors are coupled to said center-tapped transformer.

* * * * *

UNITED STATES PATENT AND TRADEMARK OFFICE
CERTIFICATE OF CORRECTION

PATENT NO. : 4,686,991

DATED : August 18, 1987

INVENTOR(S) : Joel R. Dufresne and Alan P. Dieken

It is certified that error appears in the above-identified patent and that said Letters Patent is hereby corrected as shown below:

Col. 1, line 54, "effeciency" should read --efficiency--.

In the Drawings

In Figures 2 and 4 please add the label --TCVR-- to block 60.

In Figure 2, please add the symbol --+-- next to the symbol "V" near element 76.

In Figure 2, please correct the identification of the winding 36 of transformer 38 by moving the dot from the end of the winding going to element 28 to the end of the element going to "+V".

In Figure 4, please add the symbol --+-- next to the symbol "+V" near elements 12, 38, 56, 58, 84 and 88.

Signed and Sealed this

Twenty-fourth Day of May, 1988

Attest:

DONALD J. QUIGG

*Attesting Officer*      *Commissioner of Patents and Trademarks*